United States Patent [19]
Doyle

[11] 3,935,859

[45] Feb. 3, 1976

[54] SURGICAL NASAL SPLINT

[76] Inventor: Donald E. Doyle, 8147 Amor Road, Los Angeles, Calif. 90046

[22] Filed: Sept. 16, 1974

[21] Appl. No.: 506,401

[52] U.S. Cl. ............................... 128/89 R; 128/342
[51] Int. Cl.² ............................................ A61F 5/04
[58] Field of Search.......... 128/89, 83, 87, 342–348, 128/270, 325

[56] References Cited
UNITED STATES PATENTS

| | | | |
|---|---|---|---|
| 1,256,188 | 2/1918 | Wilson | 128/342 |
| 2,010,485 | 8/1935 | Heath | 128/342 |
| 2,265,387 | 12/1941 | McMillin | 128/342 X |
| 2,335,936 | 12/1943 | Hanlon | 128/342 |

*Primary Examiner*—Robert W. Michell
*Assistant Examiner*—J. Yasko
*Attorney, Agent, or Firm*—Flam & Flam

[57] ABSTRACT

A one piece plastic nasal splint is presized to fit the nasal passage, an isthmus bridging the columella to provide anterior fixation while a single suture provides posterior fixation.

7 Claims, 5 Drawing Figures

U.S. Patent   February 3, 1976   3,935,859
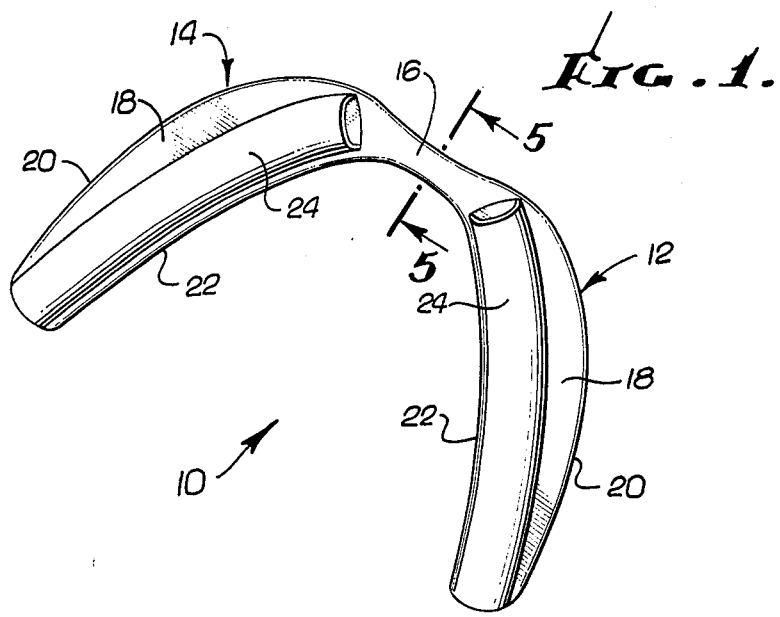
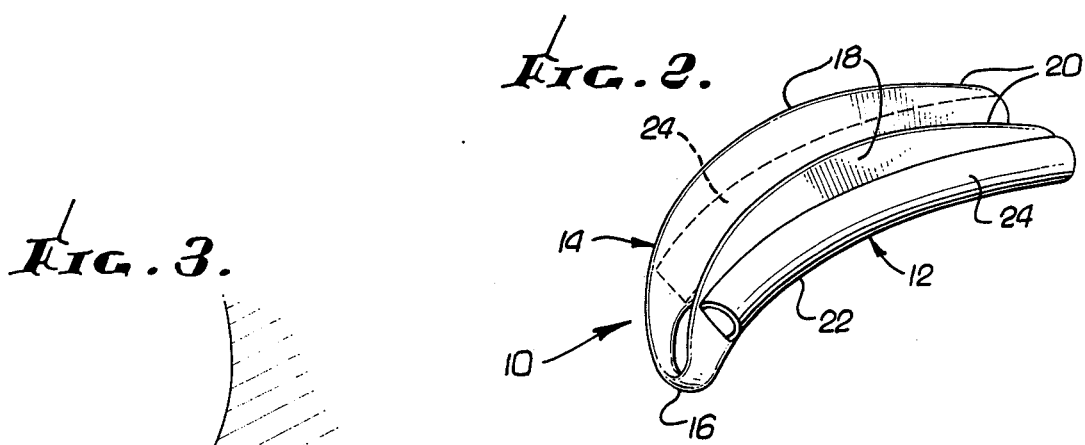
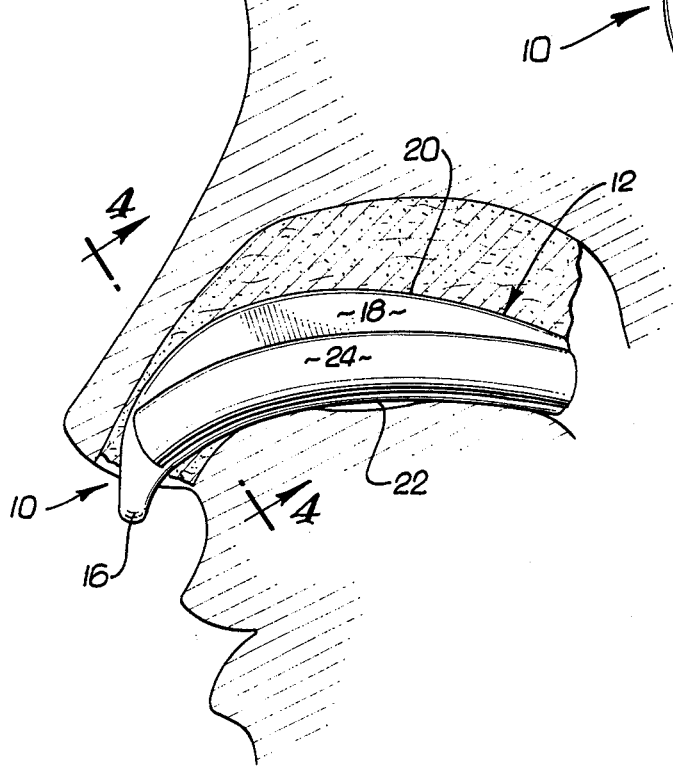
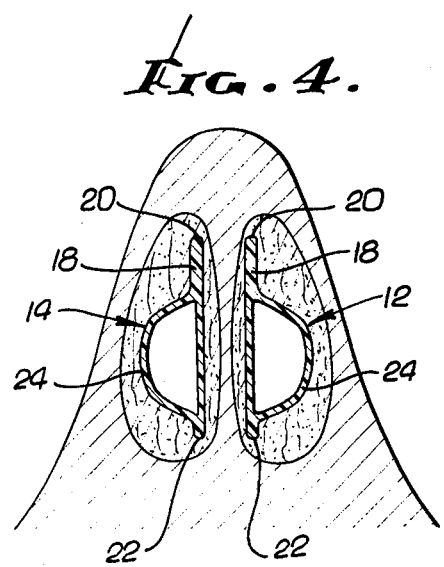

SURGICAL NASAL SPLINT

FIELD OF INVENTION

This invention relates to nasal surgery, and particularly to a post operative splint.

BACKGROUND OF THE INVENTION

Patients who have undergone septal reconstruction frequently lose midplane orientation of the septum notwithstanding optimum placement at the conclusion of surgery. Healing, of course, requires a period of days and weeks. Even slight asymmetrical pressures during the healing period may result in undesired distortions. It is possible that a patient originally suffering from septal deviation will not remain corrected following surgery.

Nasal surgery ordinarily requires a tight packing in order to control bleeding. Such packing interferes with normal nasal breathing and imposes an unphysiologic oral breathing. Sustained mouth breathing dries the mouth and results in discomfort, possibly more painful than the perinasal post-operative pain.

Rhinologic surgeons have attempted the use of septal splints both with and without breathing passages. Commonly, plastic sheets are cut to fit at the time of surgery and are sutured in place. My experience has been that these splints work loose. Cutting and stabbing sensations are encountered.

OBJECTS AND SUMMARY OF INVENTION

The primary object of the present invention is to provide an improved nasal splint for surgical use. For this purpose, I provide a one piece plastic splint presized to fit the nasal cavities. The splint limbs or elements for the nostrils are joined at an isthmus that embraces the columella. This provides an anterior anchor or fixation without the necessity of sutures. Furthermore, the isthmus positively prevents the potentially fatal aspiration that might otherwise occur by dislodgement of an anterior suture. A deeply placed posterior suture provides a second spaced fixation.

The splint limbs or elements each have a breathing passage that remains unoccluded as nasal packing is added. The presized splints have rounded edges that provide maximum comfort under the circumstances. However, the plastic material yet can be cut if special contour is required at the time of surgery.

The splint stabilized the septum and surrounding tissues and provides immobilization during healing. When properly placed, the danger of hematoma formation is virtually eliminated. The breathing passages, if clogged, are easily cleaned by aspiration or other simple procedures.

BRIEF DESCRIPTION OF THE DRAWINGS

A detailed description of the invention will be made with reference to the accompanying drawings wherein like numerals designate corresponding parts in the several figures. These drawings, unless described as diagrammatic, or unless otherwise indicated, are to scale.

FIG. 1 is a pictorial view of a nasal splint incorporating the present invention.

FIG. 2 is a pictorial view of the nasal splint flexed in preparation for insertion into the nasal cavities.

FIG. 3 is a side elevational view of the splint in place, the surrounding anatomy of the patient being diagrammatically illustrated.

FIG. 4 is an enlarged transverse sectional view of the splint in place, and taken along a plane corresponding to line 4—4 of FIG. 3, the patient anatomy being likewise illustrated.

FIG. 5 is a section view through the isthmus, and taken along a plane corresponding to line 5—5 of FIG. 1.

DETAILED DESCRIPTION OF THE PREFERRED EMBODIMENT

The following detailed description is of the best presently contemplated mode of carrying out the invention. This description is not to be taken in a limiting sense, but is made merely for purposes of illustrating the general principles of the invention since the scope of the invention is best defined by the appended claims.

The nasal splint 10 comprises two symmetrical limbs or elements 12 and 14 joined by a bridging member or isthmus 16. Each of the limbs has a flat plate part 18 having a contour designed to fit the septum of the user. The plate part has a top edge 20 convexly curved and a lower edge 22 that is nearly straight, or only slightly concavely curved. The edges approach each other at a narrowed anterior or frontal end of the splint limb and likewise approach each other at the posterior or rearward end of the limb. The maximum transverse dimension is medially located to correspond to the main region of the septum.

The anterior ends of the plate parts 18 are joined together by the bridge or isthmus 16. When the splint is to be positioned, the limbs are flexed towards each other so that flat portions of the limbs oppose each other. The posterior ends of the limbs are correspondingly positioned for conjoint insertion. With the splint positioned, the isthmus falls along the columella and limits the rearward projection of the splint. The outer sides of each limb plate has a breathing tube 24 integrally formed therewith that extends substantially the entire length of the splint limb. The splint is positioned as shown in FIGS. 3 and 4. Preferably, one or two layers of guaze 26 forms a pad between the septum and the splint plate 18. When first positioned, a suture at the posterior end fixes the splint to the septum. Thereafter, gauze on the outside of the splint limbs fully pack the nose. Generally the gauze is saturated with petroleum jelly.

The edges 20 and 22 are rounded as is the isthmus itself (FIG. 5). The splint when positioned imposes the least possible amount of discomfort. Breathing through the nose is made possible notwithstanding tight gauze packing. The septum is stabilized during the healing process and accurate midplane positioning of the septum can be expected notwithstanding extensive reconstruction.

The splint is preferably made in one piece by molding of a suitable flexible plastic material such as polyvinyl chloride. This material, especially when reinforced by the curved breathing tubes 24, exhibits sufficient characteristics of rigidity to perform the intended splint function. Other materials, of course, can be provided. In any event, the material is soft enough to allow its suturing. Instead of molding, the splint can, of course, be fabricated by welding components together. Surgical splints can be provided in a few standard sizes so that cutting and fitting at the time of surgery is largely avoided.

Intending to claim all novel, useful and unobvious features shown or described, I claim:

1. A surgical nasal septum splint made of one piece of flexible material, and characterized by two splint limbs having anterior ends joined together by an isthmus adapted to underlie the columella of the patient to provide an anchor to preclude accidental aspiration, and having free posterior ends for conjoint nasal insertion, each of the limbs having a flat inside surface to fit against the nasal septum.

2. The splint as set forth in claim 1 in which said limbs each have an integral breathing tube extending substantially the length of the corresponding limb, said tube being sufficiently rigid to remain open notwithstanding tight packing for hemostasis.

3. The splint as set forth in claim 2 in which the flat inside surfaces of said limbs each generally conform to the configuration of the human septum.

4. The splint as set forth in claim 2 in which each of said limbs at its upper end is convexly curved and of reduced transverse dimension to facilitate placement in the nasal passage.

5. The splint as set forth in claim 4 in which the said isthmus is rounded to minimize discomfort to the patient.

6. The process of stabilizing the septum of a patient following nasal reconstruction, which comprises placing a one piece splint in the two nasal passages of the patient leaving an anterior bridge or isthmus part of the splint at the columella; thereafter suturing only the posterior end of the splint to the septum.

7. The process as set forth in claim 6 in which said splint is provided with breathing tubes for both passages, said process being further characterized by the step of packing the nasal passages following said suturing with gauze or equivalent material.

* * * * *